United States Patent [19]

McLane

[11] Patent Number: Plant 5,548

[45] Date of Patent: Sep. 3, 1985

[54] *HYGROPHILA POLYSPERMA* TROPIC SUNSET

[76] Inventor: Bradford G. McLane, 700 S. Flamingo Rd., Fort Lauderdale, Fla. 33325

[21] Appl. No.: 512,426

[22] Filed: Jul. 11, 1983

[51] Int. Cl.[3] ..... A01H 5/00

[52] U.S. Cl. ..... Plt./88

[58] Field of Search ..... Plt./88

*Primary Examiner*—Robert E. Bagwill

[57] ABSTRACT

A *Hygrophila polysperma* plant characterized by leaf veins which are red in light shade and white in heavy shade, and therefore provide a color contrast with the rest of the leaf, which is green.

3 Drawing Figures

1

DESCRIPTION OF THE INVENTION

This invention relates to a new and distinct variety of *Hygrophila polysperma* entitled Tropic Sunset.

*Hygrophila polysperma* is an aquatic plant which is native to southeast Asia. It does not seed or flower in the United States, to my knowledge.

*In Hygrophila polysperma* plants cultivated aquatically by me in Fort Lauderdale, Fla., I discovered a sport thrown by one of these plants which was characterized by the novel coloring of the veins in its leaves. I took cuttings from this sport and have asexually reproduced my new variety by re-rooting the cuttings in Fort Lauderdale, Fla.

2

Figure 1:
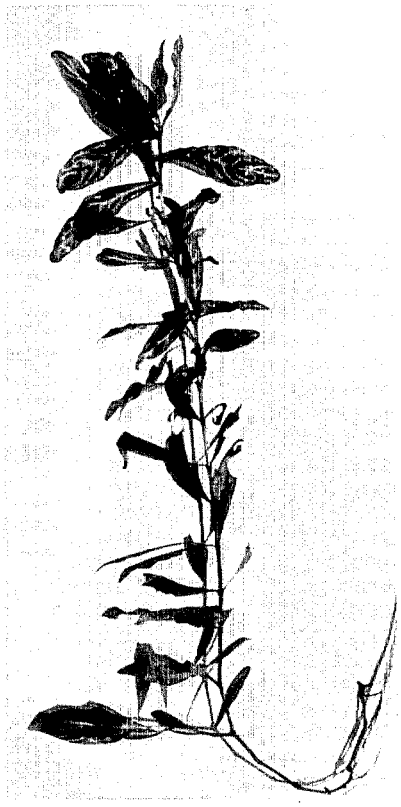
FIG. 1 shows one of my new variety of *Hygrophila polysperma* removed from the water.
Figure 2:
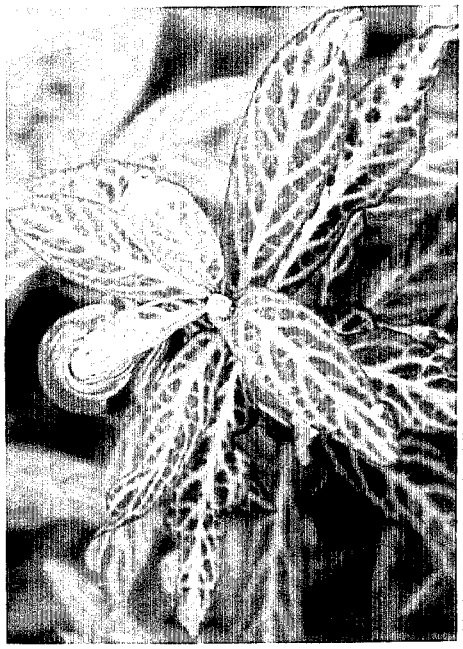
FIG. 2 shows the appearance of the leaves in light (approximately 60%) shade, where the leaf veins are red.
Figure 3:
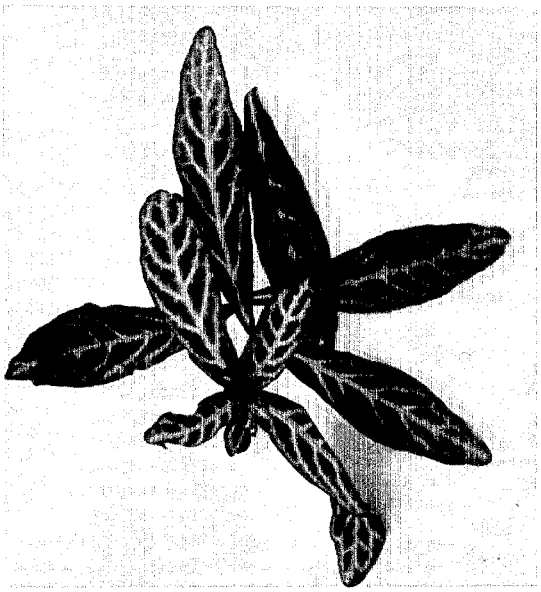
FIG. 3 shows the appearance of the leaves in heavy (approximately 90%) shade, where the leaf veins are white.

In both light and heavy shade the leaf appearance is very different from the previously known *Hygrophila polysperma,* which has green veins in the leaf and little color contrast between the veins and the rest of the leaf. In my new variety, the decorative appearance of the leaf is improved by the color contrast between the prominent veins and the rest of the leaf. This color contrast changes when my new variety is moved from light shade to heavy shade, or vice versa, and this characteristic enhances the versatility with which it can be displayed. The different color of the veins apparently is due to a loss of green chlorophyll pigment. The vein color ranges from 55A through 55D as shown in The R.H.S. Colour Chart.

Except for the distinctive coloring of the veins in the leaves, my new variety is essentially the same as the previously known *Hygrophila polysperma.*

I claim:

1. A new and distinct variety of *Hygrophila polysperma* plant as described and illustrated, characterized by leaves whose veins are red under low shade and white under heavy shade.

* * * * *